:::

United States Patent
Orlowski et al.

(12)
(10) Patent No.: US 6,447,757 B1
(45) Date of Patent: Sep. 10, 2002

(54) TEETH WHITENING COMPOSITION WITH INCREASED BLEACHING EFFICIENCY AND STORAGE STABILITY

(75) Inventors: Jan A. Orlowski, Altadena; David V. Butler, West Covina; Amy P. Noss, Arcadia, all of CA (US)

(73) Assignee: Scientific Pharmaceuticals, Inc., Pomona, CA (US)

( * ) Notice: Subject to any disclaimer, the term of this patent is extended or adjusted under 35 U.S.C. 154(b) by 7 days.

(21) Appl. No.: 09/709,061

(22) Filed: Nov. 8, 2000

(51) Int. Cl.[7] .............................. A61K 7/16; A61K 7/20
(52) U.S. Cl. ........................................ 424/53; 424/49
(58) Field of Search ............................................ 424/53

(56) References Cited

U.S. PATENT DOCUMENTS

| | | | |
|---|---|---|---|
| 3,657,413 A | 4/1972 | Rosenthal | |
| 4,032,627 A | 6/1977 | Suchan et al. | |
| 4,405,599 A | 9/1983 | Smigel | |
| 4,522,805 A | 6/1985 | Gordon | |
| 4,661,070 A | 4/1987 | Friedman | |
| 4,687,663 A | 8/1987 | Schaeffer | |
| 4,788,052 A | 11/1988 | Ng et al. | |
| 4,895,721 A | 1/1990 | Drucker | |
| 4,897,258 A | 1/1990 | Rudy et al. | |
| 4,971,782 A | 11/1990 | Rudy et al. | |
| 4,976,955 A | 12/1990 | Libin | |
| 4,980,154 A | 12/1990 | Gordon | |
| 4,983,379 A | 1/1991 | Schaeffer | |
| 5,000,942 A | 3/1991 | Libin | |
| 5,041,280 A | 8/1991 | Smigel | |
| 5,076,791 A | 12/1991 | Madray, Jr. | |
| 5,171,564 A | 12/1992 | Nathoo et al. | |
| RE34,196 E | 3/1993 | Munro | |
| 5,240,415 A | 8/1993 | Haynie | |
| 5,264,205 A | 11/1993 | Kelly | |
| 5,356,291 A | 10/1994 | Darnell | |
| 5,376,006 A | 12/1994 | Fischer | |
| 5,437,858 A | 8/1995 | Hungerbach et al. | |
| 5,597,554 A | 1/1997 | Wagner | |
| 5,645,821 A | 7/1997 | Libin | |
| 5,648,064 A | * 7/1997 | Gaffar et al. | 424/53 |
| 5,690,913 A | 11/1997 | Hsu et al. | |
| 5,698,182 A | 12/1997 | Prencipe et al. | |
| 5,746,598 A | 5/1998 | Fischer | |
| 5,851,514 A | * 12/1998 | Hassan et al. | 424/53 |
| 5,858,332 A | 1/1999 | Jensen et al. | |
| 5,902,568 A | 5/1999 | Ryles et al. | |
| 5,922,307 A | * 7/1999 | Montgomery | 424/53 |
| 5,928,628 A | 7/1999 | Pellico | |
| 6,036,493 A | 3/2000 | Sharma | |
| 6,106,293 A | 8/2000 | Wiesel | |
| 6,106,812 A | * 8/2000 | Prencipe et al. | 424/53 |
| 6,149,895 A | 11/2000 | Kutsch | |
| 6,312,670 B1 | * 11/2001 | Montgomery | 424/53 |
| 6,322,773 B1 | * 11/2001 | Montgomery | 424/53 |

OTHER PUBLICATIONS

Daytime Zero Sensitivity Tooth Whitening Advertisement, 1 page.
Nite White Excel2 Advertisement, 1 page.
Opalescence PF Advertisement, 1 page.
Opalescence Tooth Whitening System, A Reason to Smile Advertisement, 2 pp.
Opalescence Dentist Instructions, 6 pp.

* cited by examiner

Primary Examiner—Shep K. Rose
(74) Attorney, Agent, or Firm—Knobbe, Martens, Olson & Bear, LLP.

(57) ABSTRACT

Disclosed are compositions for bleaching teeth comprising at least two parts blended together before each application. The compositions offer extended shelf life and accelerated bleaching action while significantly reducing the possibility of user discomfort. In preferred embodiments, one part of the composition comprises peroxides of monovalent or bivalent metals such as sodium, potassium, magnesium, calcium, strontium, and zinc, and another part comprises an aqueous solution of one or more acids able to convert said metal peroxides into hydrogen peroxide, such reaction occurring under conditions resulting in the acceleration of the generation of radical oxygen and, consequently, the teeth whitening process. The inventive compositions allow for adequate water in the composition to avoid tissue desiccation and associated user discomfort without compromising the shelf life of the composition.

33 Claims, No Drawings

TEETH WHITENING COMPOSITION WITH INCREASED BLEACHING EFFICIENCY AND STORAGE STABILITY

BACKGROUND OF THE INVENTION

This invention relates generally to teeth whiteners, specifically to teeth whiteners having increased storage stability while having superior bleaching efficiency.

Teeth whiteners, also known as teeth bleaching agents, are in widespread use as a cosmetic means to enhance appearance and contribute to better oral health and hygiene in general. Particularly popular and effective among these agents are those whose chemistry is based on peroxides, of which hydrogen peroxide and carbamide peroxide (an adduct of hydrogen peroxide and urea) are most frequently employed. Such peroxides are characterized by a relative lack of stability which results in the generation of radical (atomic) oxygen, the chemical action of which is responsible for the desired whitening/bleaching effect of whitening agents containing such peroxides. The generation of atomic oxygen is highly undesirable during storage of peroxide-based teeth whitening agents because it reduces the potency of the agent in that some of the peroxide decomposes prior to the time of use. Thus, in their commercial form, whitening agents are formulated and/or stored in a manner designed to prevent and/or inhibit premature peroxide decomposition. Because contact with certain foreign objects, especially materials having highly developed surface areas, exposure to selected chemicals, and the presence of an elevated pH accelerate the decomposition process of said peroxides and the liberation of radical oxygen, attempts are made to avoid such conditions.

Stability of teeth whitening formulations, however, is in direct conflict with the purpose and objective of their applications, in that the best possible whitening effect in the shortest possible time of contact with the tooth surface is achieved when the composition, when placed in contact with the teeth, is very unstable as to evolve the radical oxygen in a reasonably short time. Consequently, teeth whitening formulations known in the art typically require multiple applications stretching over a period of weeks or even months, with each recommended application time usually being from two to eight hours.

To address this conflict between stability and efficacy, two component formulations have been recently developed to improve the stability of peroxide during storage. Such formulations allow for extended shelf life and more effective bleaching action, as the decomposition of peroxide (generation of radical oxygen) does not begin to occur at a significant rate until the two components are mixed.

In one type of two component system, the first component contains peroxide and is maintained at a low pH and is free of solid particles. Formulations based on carbamide peroxide are preferably water free as well to further enhance stability. The second component contains materials that stimulate the decomposition of peroxides, such as alkaline substances and insoluble particles having highly developed surface areas. The second part generally contains water in order to reduce tissue irritation caused by the desiccating effect of anhydrous and hydrophilic mediums used in the first part which would tend to draw water out of the mucosa and other oral tissues when placed in the mouth.

Of the two forms of peroxides commonly used in commercial teeth whiteners, hydrogen peroxide formulations are considered to be faster acting, while carbamide peroxide based formulations are considered to offer advantages in terms of greater storage stability, desirable formulation consistency and handling properties, and a lower risk of damage to soft tissues. Both hydrogen peroxide and carbamide peroxide-based formulations are more stable at low pH, preferably in the range of 3.0–4.5, with this effect being more pronounced in hydrogen peroxide formulations. Carbamide peroxide-based materials may, however, exhibit adequate stability even at neutral or near neutral pH. Because of these properties, formulations containing carbamide peroxide may be perceived as more desirable in terms of exhibiting greater compatibility with mucosa, having little or no detrimental effect on tooth enamel, and aiding in protecting the health of teeth in less than intact condition.

Carbamide peroxide formulations are, however, adequately stable only in environments containing little or no water. Examples of common commercial carriers for carbamide peroxide are glycerin and propylene glycol. While such carriers are considered nontoxic and convenient for their compatibility with desirable additives such as thickening agents, preservatives, flavors and therapeutics, their use may have some unwelcome side effects. The most common side effect is discomfort caused by the desiccating effect of these anhydrous (or near anhydrous) yet hydrophilic solvents/carriers on mucosa, as discussed above. This effect is especially pronounced when scarified or inflamed tissue is involved. Similar responses of discomfort may also be expected by those having leaching restorations or recessed gums.

The concentrations of peroxides in commercially available teeth bleaching formulations vary greatly, generally depending on factors such as recommended time of a single application, frequency and technique of application, and the identity of the intended user. This last factor is especially important, in that the concentration of peroxide will differ if the material is designed for professional use only, for application by the user/patient but under professional control, or if it is to be broadly available to the public for in-home, non-supervised use.

The concentration of peroxide (expressed as a percentage of $H_2O_2$) in formulations containing carbamide peroxide or hydrogen peroxide which are sold directly to the public is generally on the order of 3.4% by weight, which corresponds to approximately 10% carbamide peroxide. The concentration of $H_2O_2$ in formulations designed for professional use is generally higher, and often lies in the 5–10% range.

To provide prolonged contact of whitening formulation with teeth while minimizing contact with mucosa which may cause irritation, the whitening material is usually placed on fabricated trays, preferably those which have been custom fit in a dentist's office to precisely conform to the patient's anatomy. The use of more highly concentrated $H_2O_2$ formulations, which are generally faster acting, calls for special measures to protect the mucosa from contact with such inherently irritating compositions. In such cases, rubber dams or curable tissue coatings are routinely used to protect soft tissues.

Attempts have been made to accelerate the teeth bleaching processes without increasing the concentration of the peroxide by using heat-generating devices such as high intensity light emitting instruments or lasers. Because of the cost of necessary equipment and the greatly increased risk of tissue damage associated with these techniques, they are designed for use exclusively by a trained dental professional. The most effective of these techniques appear to be those using lasers, but such techniques also carry the highest risk of inflicting damage on the teeth and/or soft tissue. Furthermore, the treatment cost is considerably higher than when conventional methods are used.

SUMMARY OF THE INVENTION

Disclosed are new teeth whitening compositions comprising at least two components which are separated from one another during storage. The components are mixed shortly or immediately before their application to the teeth. In accordance with one aspect of the present invention, there is provided a teeth whitening composition comprising a first component, Part 1, comprising 5–40% by weight of at least one metal peroxide and a second component, Part 2, comprising at least one acid, wherein the Part 1 and Part 2 are mixed together shortly or immediately before application to form a material having a pH of about 4 to 11. In preferred embodiments, Part 1 comprises one or more peroxides of monovalent or bivalent metals, preferably zinc, sodium, calcium, magnesium, potassium, strontium, and combinations thereof, and Part 2 comprises organic and/or inorganic acids able to convert such peroxides of the first component to hydrogen peroxide. Parts 1 and/or 2 of the whitening compositions may further comprise thickening agents, fillers, dyes, flavorings, indicators, fluoride or other additives, and/or combinations thereof. Preferred whitening compositions are characterized, in part, by their ability to generate atomic (radical) oxygen at a significantly faster rate than is possible in conventional hydrogen peroxide or carbamide peroxide based teeth whitening systems known in the art.

In accordance with a further aspect of the present invention, there is provided a teeth whitening procedure, comprising preparing a teeth whitening composition comprising mixing a first part comprising 5–40% by weight of at least one metal peroxide and a second part comprising at least one acid to form a material having a pH of about 4 to 11, and applying the teeth whitening composition to the teeth. In preferred embodiments, the application is by means of flexible trays or forms, by a toothbrush, or by a freehand technique.

DETAILED DESCRIPTION OF THE PREFERRED EMBODIMENTS

As discussed above, prior art formulations for teeth whitening tend to have one or more difficulties or shortcomings, rendering them ineffective or undesirable. Many of the difficulties arise from the inherent conflict between the requirements of shelf life stability of peroxides and the understandable demand for fast bleaching action and high efficacy of the product. Part of this conflict arises from the fact that storage stability requirements impose the necessity of maintaining low pH on commercial teeth whitening formulations, especially those based on hydrogen peroxide, which is objectionable from the point of view of the potentially damaging effect of such acidic materials on teeth and mucosa and the slow generation of radical (atomic) oxygen in the oral environment which impairs the speed and efficacy of the teeth bleaching process. On the other hand, some more recent two component teeth bleaching formulations containing either hydrogen peroxide or carbamide peroxide as the active ingredient require the use of highly alkaline materials to bring the pH of the final mixture above 11. Such alkaline materials could cause irritation of mucosa, especially in cases of scarified or inflamed tissue.

The present invention looks to overcome some or all of the shortcomings of the prior art formulations as discussed above. In preferred embodiments, the present invention provides fast acting teeth whitening compositions that minimize tissue desiccation, are substantially insensitive to ambient temperatures, and are not compromised by unduly short shelf lives.

The present invention relates to a new teeth whitening system comprising at least two parts separated from each other during storage. In a preferred two component embodiment, the two components, referred to herein as Part 1 and Part 2, are preferably mixed shortly or immediately before application. Although the present invention is described and exemplified herein by means of a two component preferred embodiment, it is to be understood that the invention is intended to cover formulations comprising more than two components. As used herein "shortly before application" means about 20–30 minutes before application and "immediately before application" means within about 5 minutes of application. The whitener may still be used more than 30 minutes after mixing, but, due to peroxide decomposition, some or most of its whitening effectiveness may be absent.

The first component, Part 1, is preferably of a gel or paste consistency. Thickeners and/or fillers may be added to achieve this consistency. Part 1 comprises one or more metal peroxide, preferably those of monovalent or divalent metals. Preferred peroxides include calcium peroxide, zinc peroxide, and sodium peroxide, with other peroxides including, but not limited to, those of potassium, magnesium, and strontium also being suitable for use in the inventive formulations. The peroxide is suspended or dispersed in a medium to form a mixture which is preferably 5–40% metal peroxide by weight, more preferably 15–30% peroxide by weight, most preferably 20%. In an alternative embodiment, the mixture is 2–16% peroxide by weight, more preferably 6–10% peroxide by weight. The component may further comprise one or more additives to modify rheology, texture, flavor, fragrance, color, or other properties. Preferred media for use in Part 1 include glycerin, propylene glycol, polyethylene and/or polypropylene glycols, water, and mixtures of the foregoing. In some embodiments alcohol is added to the media.

In an alternate embodiment, the first component, the metal peroxide of Part 1, is suspended or dispersed in a liquid to form a mixture which is preferably 8 to 25% by weight of peroxide, more preferably 8–15%.

Part 2 comprises a solution of one or more acids in water or aqueous solution which may be modified to achieve a desired consistency, such as that of a gel or paste, by the addition of thickeners and/or fillers. Preferred acids include organic acids including acetic acid, tartaric acid, phosphoric acid, and citric acid. The total acid concentration in Part 2 is preferably 30 to 100% of the stoichiometric requirement to convert metal peroxides to their salts and hydrogen peroxide, more preferably 50 to 80% of the stoichiometric requirement. Preferred thickening agents include xantham gum, polyacrylic acid, and cellulose derivatives (e.g. carboxymethylcellulose) and preferred fillers include silica, diatomaceous earth, alumina, and powdered polyethylene or polypropylene or other polymers. The thickeners and/or fillers are added in a quantity sufficient to achieve the desired consistency. These same thickeners and fillers may also be used as additives in Part 1. Additives to modify rheology, texture, flavor, fragrance, and color may also be present in Part 2. In addition, alcohol or other water miscible solvents may be added to Part 2.

Parts 1 and 2 are preferably mixed in equal proportions to form the whitening formulation, although the ratio may vary from 1:1 depending primarily on the concentrations of peroxide in Part 1 and acid in Part 2. Preferably, stoichiometric proportions of alkaline and acid components should be employed such that the resulting mix has a moderately alkaline pH. The pH of the blend or mixture of Parts 1 and 2 is preferably between about 4 and 12, more preferably between about 8 and 12, most preferably between about 8 and 10. The presence of silica or similar finely divided particles having highly developed surface areas is particularly desirable due to the acceleration of the decomposition of peroxide and subsequent generation of radical oxygen contributed by the presence of these materials. The rate of generation of radical oxygen is an important component in achieving desirable whitening effects in shortened application times.

Once combined, the peroxide of Part 1 reacts with the aqueous acid of Part 2 to generate hydrogen peroxide in situ, which in turn generates radical or atomic oxygen. Although it is believed that most of the peroxide will pass through the hydrogen peroxide intermediate, the generation of such an intermediate prior to the formation of radical or atomic oxygen is not critical to the present invention. It was entirely unexpected that by generating hydrogen peroxide in situ as a reaction product of metal peroxides of sodium, potassium, magnesium, calcium, strontium and/or zinc with acids, highly favorable conditions for teeth whitening may be created both from the point of view of the rate of the bleaching process and tissue tolerance. This allows for the elimination of relatively unstable hydrogen peroxide and its adducts from tooth whitening formulations by replacing them with a combination of thermally stable compounds that are also more tolerant of the presence of other desirable components (such as organic thickeners or fillers having highly developed surface areas). Such substitution does not change the clinically proven mechanism of teeth whitening based on hydrogen peroxide interaction with tooth enamel and dentin, as reaction occurs when the components of the system are blended together prior to placement of the whitener in the mouth, according to the general schemes:

$$Me_2O_2 + 2HR_{(aq)} \rightarrow 2MeR + H_2O_2$$

$$MeO_2 + 2HR_{(aq)} \rightarrow MeR_2 + H_2O_2$$

Where H represents hydrogen, O represents oxygen, R is the acidic anion, and Me represents metals. The first example concerns monovalent metals and the second bivalent metals.

Hydrogen peroxide, being much less stable than metal peroxides, then undergoes accelerated decomposition in the presence of chemical components of the device, and/or reaction products resulting from such components coming into contact with saliva, which act as catalysts in the reaction below:

$$H_2O_2 \rightarrow H_2O + O$$

Byproducts of the bleaching process of this invention are salts of alkaline and alkaline earth metals with acids preferably having an alkaline character. Such salts were found to accelerate the decomposition of hydrogen peroxide resulting in the liberation of radical oxygen and thus further accelerating the teeth bleaching process. This acceleration results from two independent factors: first, such salts represent fine solid particles having highly developed surface areas; and second, the alkaline nature of such salts raises the pH, resulting in an environment that is highly unfavorable to the stability of hydrogen peroxide.

Formulations of the present invention are hydrous because hydrogen peroxide is commercially available only in aqueous solutions. Additional water is generated as a result of reactions occurring during the bleaching process, resulting in formulations that contain more than sufficient water to prevent or minimize tissue desiccation and thus reduce soft tissue irritation. Calcium salts generated during the synthesis of hydrogen peroxide also have a mineralizing effect on enamel and dentin, further enhancing the whitening effect and contributing to the improved health of oral hard tissues.

Unlike hydrogen peroxide and its adducts, including carbamide peroxide, the peroxides of metals belong to the first and second groups of the periodic table are generally stable even at moderately elevated temperatures. Moreover, surprisingly, such peroxides remain stable when in contact with materials known to be affected by or to degrade hydrogen peroxide and its complexes. This includes such otherwise desirable components of teeth whitening formulations as commonly used organic rheological agents and thickeners such as natural gums and cellulose derivatives, flavoring agents, fillers, and colorants. Thermal stability of the teeth whitening materials involving preservation of the original chemical make-up, consistency, flavor and appearance increases their effectiveness and commercial acceptance.

Unlike prior art carbamide peroxide formulations which must be anhydrous or nearly anhydrous to provide adequate shelf life stability, the formulations of the present invention are based on water or aqueous media and therefore should not cause the type of user discomfort associated with the dehydration of oral tissues that results from the use of anhydrous formulations. In addition, due to the greater thermal stability of selected peroxides, particularly calcium peroxide, and their compatibility with water, glycerin, alcohols, and other dispersing mediums acceptable for intraoral applications, the teeth whitening system according to preferred embodiments of this invention is, in contrast to prior art systems based on hydrogen or carbamide peroxides, virtually insensitive or substantially less sensitive to storage conditions.

In contrast to other fast action teeth whitening systems, no special instruments are necessary or indicated in relation with the teeth whitening process of this invention.

As mentioned above, other components or additives may be added to either or both of Parts 1 and 2. For example, incorporation of fluoride salts such as stannous fluoride, sodium monofluorophosphate or sodium fluoride at a concentration corresponding to 100–2000 ppm of fluoride in the mixed composition may add additional benefits to the teeth treatments of this invention. Flavoring and coloring agents may be added to enhance the acceptance or appeal of the material, or as indicators of the reactivity of peroxide and the progress of radical oxygen generation. Any flavoring may be used, including fruit flavors and flavors normally associated with foods or candies, with the most desirable flavors including, among others, food grade orange, lemon, peppermint, spearmint, mint, bubble gum, cherry, watermelon, strawberry and apple varieties. As coloring agents, FD&C or D&C water soluble dyes may be used; with FD&C Blue #1 and FD&C Blue #2 being preferred. In some formulations, the color is chosen in accordance with the flavoring (e.g. red coloring being used with cherry flavor). Coloring and/or flavoring agents may be incorporated into either or both parts of the system.

Once combined, the mixture of Parts 1 and 2 can be applied to teeth by any means commonly employed in the teeth whitening arts, including custom formed trays, a toothbrush, or by using the, free-hand technique to apply the material to the teeth by means of a swab, brush, stick, or other applicator.

Once applied, the composition is allowed to remain in contact with the teeth for at least 5 minutes, preferably it remains in contact with the teeth for about 15 to 120 minutes, more preferably about 20 to 60 minutes. In a preferred whitening procedure, the application of whitener is repeated about 2 to 14 times, with each application coming no more than twice a day.

The following examples use decolorization of the dye FD&C Blue #1 to exhibit the bleaching action of the teeth whitening mixtures. After Parts 1 and 2 are mixed, decolorization of the FD&C blue is monitored. In one embodiment, these dyes are added to the preparations to monitor how long the patient needs to leave the preparation in contact with his/her teeth. When the blue color disappears or is substantially reduced, the patient can assume that the teeth bleaching activity has occurred.

EXAMPLES

Selected embodiments of this invention are illustrated in Examples 1–14 below:

Example 1

The teeth bleaching system consisted of:

| Part 1: | | | |
|---|---|---|---|
| calcium peroxide | 20.01 g | | |
| glycerin | 68.96 g | | |
| sodium polyacrylate | 6.03 g | | |
| silica | 5.00 g | | |
| Part 2: | | | |
| water | 61.25 g | silica | 8.74 g |
| acidic mixture: | 21.44 g | ethyl alcohol | 6.12 g |
| citric acid | 9.19 g | polyethylene oxide | 2.45 g |
| phosphoric acid | 9.19 g | FD&C Blue #1 | 1 drop |
| acetic acid | 3.06 g | | |

The parts were mixed together in a 1:1 ratio on a volumetric basis. The pH of the mixture was pH 5.39 at 24.9° C. The material, which originally was blue due to incorporation of one drop of FD&C Blue #1, became whitish after 24 hours.

Example 2

The bleaching system consisted of two parts:

| Part 1: | | | |
|---|---|---|---|
| calcium peroxide | 30.00 g | | |
| glycerin | 62.84 g | | |
| sodium polyacrylate | 7.16 g | | |
| Part 2: | | | |
| water | 54.20 g | silica | 7.21 g |
| acidic mixture: | 31.01 g | ethyl alcohol | 5.42 g |
| citric acid | 12.04 g | polyethylene oxide | 2.16 g |
| phosphoric acid | 8.13 g | FD&C Blue #1 | 1 drop |
| acetic acid | 10.84 g | | |

After the parts were mixed together in a 1:1 ratio on a volumetric basis, the pH of the blend was 5.53 at 24.5° C. The blue color disappeared entirely within 18 hours.

Example 3

| Part 1: | | | |
|---|---|---|---|
| calcium peroxide | 20.00 g | | |
| glycerin | 35.47 g | | |
| water | 35.47 g | | |
| silica | 7.28 g | | |
| carboxymethylcellulose | 1.78 g | | |
| Part 2: | | | |
| water | 61.45 g | silica | 8.30 g |
| acidic mixture: | 21.55 g | isopropanol | 6.15 g |
| citric acid | 9.21 g | polyethylene oxide | 2.46 g |
| phosphoric acid | 9.21 g | methyl paraben | 0.09 g |
| acetic acid | 3.13 g | BHT | 0.0009 g |
| | | FD&C Blue #1 | 1 drop |

When Part 1 from this example was combined with the Part 2 described in Example 1, the material was essentially uncolored (white) within 18 hours; when mixed with the Part 2 of Example 2, it was white within 4 hours; and when mixed with the Part 2 described above the time for elimination of the blue coloration was less than 3 hours.

Example 4

| Part 1: | |
|---|---|
| calcium peroxide | 30.00 g |
| glycerin | 31.04 g |
| water | 31.04 g |
| silica | 6.35 g |
| carboxymethylcellulose | 1.57 g |

Part 1 was combined with three different Part 2 formulations: those from Example 1, Example 2 and Example 3. The blue coloration of the initial mixture was eliminated in less than 3 hours in all cases.

Example 5

| Part 1: | |
|---|---|
| calcium peroxide | 17.0 g |
| glycerin | 37.63 g |
| water | 37.63 g |
| silica | 5.17 g |
| carboxymethylcellulose | 2.27 g |
| sodium fluoride | 0.30 g |

Part 2 was the same as used in Example 3. The pH of the material mixed in a 1:1 ratio (volumetrically) was 5.44 at 23.9° C. The material changed from blue to white within 20 hours.

Example 6

Part 1:

| | |
|---|---|
| calcium peroxide | 30.60 g |
| glycerin | 45.59 g |
| water | 18.15 g |
| silica | 4.75 g |
| carboxymethylcellulose | 0.91 g |

Part 2:

| | | | |
|---|---|---|---|
| water | 38.54 g | silica | 6.01 g |
| xylitol | 33.95 g | isopropanol | 3.85 g |
| acidic mixture: | 13.51 g | peppermint oil | 2.55 g |
| citric acid | 5.79 g | polyethylene oxide | 1.54 g |
| phosphoric acid | 5.79 g | methyl paraben | 0.053 g |
| acetic acid | 1.92 g | BHT | 0.00053 g |
| | | FD&C Blue #1 | 1 drop |

The pH of the material mixed in a 1:1 volumetric ratio was 5.50 at 27.5° C. The material was white colored within 90 minutes.

Example 7

Part 1 was the same as used in Example 6.

Part 2:

| | | | |
|---|---|---|---|
| water | 35.33 g | silica | 5.50 g |
| xylitol | 33.95 g | isopropanol | 3.53 g |
| acidic mixture: | 17.69 g | peppermint oil | 2.55 g |
| citric acid | 10.62 g | polyethylene oxide | 1.42 g |
| phosphoric acid | 5.31 g | methyl paraben | 0.049 g |
| acetic acid | 1.76 g | BHT | 0.00049 g |
| | | FD&C Blue #1 | 1 drop |

The pH of a 1:1 volumetric mixture of the material was 9.67 at 27.6° C. The material changed from blue to white within 15 minutes.

Example 8

Part 1 was the same as used in Example 6.

Part 2:

| | | | |
|---|---|---|---|
| xylitol | 33.95 g | silica | 5.07 g |
| water | 32.51 g | isopropanol | 3.25 g |
| acid mixture: | 21.33 g | peppermint oil | 2.55 g |
| citric acid | 14.65 g | polyethylene oxide | 1.30 g |
| phosphoric acid | 5.05 g | methyl paraben | 0.045 g |
| acetic acid | 1.63 g | BHT | 0.00045 g |
| | | FD&C Blue #1 | 1 drop |

The pH of a 1:1 volumetric mixture of the material was 9.58 at 27.1° C. The material lost its blue coloring within 15 minutes.

Example 9

Part 1:

| | |
|---|---|
| zinc peroxide | 20.00 g |
| glycerin | 75.10 g |
| neutralizer | 3.08 g |
| carbopol | 1.82 g |

Part 2 was the same as in Example 3. The pH of the 2:1 volumetric ratio (Part 1: Part 2) of materials was 4.64 at 24.4° C. The material was a very light blue after 24 hours.

Example 10

Part 1:

| | |
|---|---|
| calcium peroxide | 15.17 g |
| zinc peroxide | 1.69 g |
| glycerin | 37.78 g |
| water | 37.78 g |
| silica | 5.99 g |
| carboxymethylcellulose | 2.25 g |

Part 2:

| | | | |
|---|---|---|---|
| acidic mixture: | 57.94 g | isopropanol | 5.11 g |
| citric acid | 40.11 g | polyethylene oxide | 2.03 g |
| phosphoric acid | 17.83 g | methylparaben | 0.075 g |
| water | 25.45 g | BHT | 0.0007 g |
| silica | 9.39 g | FD&C Blue #1 | 1 drop |

The pH of the material mixed in a 1:1 volumetric ratio was 3.65 at 24.9° C. The material was a very light blue after 24 hours.

Example 11

Part 1:

| | |
|---|---|
| zinc peroxide | 14.51 g |
| sodium peroxide | 4.84 g |
| glycerin | 72.66 g |
| silica | 3.25 g |
| neutralizer | 2.98 g |
| carbopol | 1.76 g |

Part 2 was the same as that used in Example 3. The pH of the 1:1 volumetric ratio of materials was 4.13 at 24.3° C. The material was a very light blue after 24 hours.

Example 12

Part 1:

| | |
|---|---|
| calcium peroxide | 12.75 g |
| strontium peroxide | 4.25 g |
| glycerin | 37.78 g |
| water | 37.78 g |
| silica | 5.17 g |
| carboxymethylcellulose | 2.27 g |

Part 2 was the same as in Example 3. The pH of the 1:1 volumetric ratio of materials was 5.26 at 24.6° C. The time required for the material to lose its blue coloring was less than 24 hours.

Example 13

Control

To further demonstrate the efficacy of the developed teeth whitening system, Part 1 of Example 5 alone was subjected to peroxide stability testing at 23° C. using FD&C Blue #1 as an indicator. The material showed signs of loss of blue coloring after 48 hours. When Part 2 of Example 3 was subjected to peroxide stability testing as described above for Part 1, no fading or discoloration was observed in over 48 hours.

Example 14

Control

A sample of commercial teeth whitening gel containing 11% carbamide peroxide and one drop of FD&C Blue #1 was tested for stability as described above at room temperature. No fading or discoloration was noticed after 6 days.

Although the present invention has been described in terms of certain preferred embodiments, other embodiments of the invention will become apparent to those of skill in the art in view of the disclosure herein. Thus, obvious changes and modifications may be made without departing from the spirit and scope of the invention. Accordingly, the scope of the invention is not intended to be limited by the foregoing, but rather to be defined only by the claims which follow.

What is claimed is:

1. A teeth whitening composition comprising:
   Part 1 comprising 5–40% by weight of at least one metal peroxide; and
   Part 2 comprising at least one acid;
      wherein the Part 1 and Part 2 are mixed together less then about 30 minutes before application to form a material having a pH of about 4 to 11.

2. The composition of claim 1, wherein Part 1 comprises 15–30% by weight of at least one metal peroxide.

3. The composition of claim 1, wherein at least Part 1 has a gel or paste consistency.

4. The composition of claim 1, wherein Part 1 and Part 2 are combined in a 1:1 volumetric ratio.

5. The composition of claim 1, wherein the metal peroxide is selected from the group consisting of calcium peroxide, sodium peroxide, magnesium peroxide, potassium peroxide, strontium peroxide, zinc peroxide, and mixtures thereof.

6. The composition of claim 1, wherein the peroxide component of Part 1 comprises calcium peroxide.

7. The composition of claim 1 wherein Part 1 comprises 5–80% by weight water.

8. The composition of claim 1, wherein Part 1 comprises 5–60% by weight glycerin, propylene glycol, or mixtures thereof.

9. The composition of claim 1, wherein Part 1 further comprises an inorganic filler selected from the group consisting of diatomaceous earth, pumice, alumina, silica, and quartz, and mixtures thereof.

10. The composition of claim 1, wherein Part 2 further comprises an inorganic filler selected from the group consisting of diatomaceous earth, pumice, alumina, silica, and quartz, and mixtures thereof.

11. The composition of claim 1, wherein Part 1 comprises a thickening agent.

12. The composition of claim 11, wherein said thickening agent is selected from the group consisting of cellulose derivatives, xantham gum, polyethylene oxide, polyglycols, and polyacrylic acid, derivatives thereof, and mixtures thereof.

13. The composition of claim 1, wherein Part 2 comprises a thickening agent.

14. The composition of claim 13, wherein said thickening agent is selected from the group consisting of cellulose derivatives, xantham gum, polyethylene oxide, polyglycols, and polyacrylic acid, derivatives thereof, and mixtures thereof.

15. The composition of claim 1, wherein the acid of Part 2 is selected from the group consisting of tartaric, citric, phosphoric, oxalic, and acetic acids, and mixtures thereof.

16. The composition of claim 1, wherein the concentration of acid in Part 2 is between 5–80% by weight.

17. The composition of claim 1, wherein Part 2 comprises 20–80% by weight water.

18. The composition of claim 1, wherein Part 1 further comprises one or more additives selected from the group consisting of flavoring agents, pigments, and dyes.

19. The composition of claim 1, wherein Part 2 further comprises one or more additives selected from the group consisting of flavoring agents, pigments, and dyes.

20. The composition of claim 1, wherein at least one of Parts 1 and 2 comprises an indicator that changes color upon exposure to radical oxygen.

21. The composition of claim 18, wherein said indicator is selected from FD&C Blue #1 or FD&C Blue #2, and mixtures thereof.

22. The composition of claim 1, wherein at least one of Parts 1 and 2 comprises sodium fluoride, stannous fluoride, or sodium monofluorophosphate at a concentration corresponding to 100–2000 ppm of fluoride in the mixed composition.

23. The composition of claim 1, wherein at least one of Parts 1 and 2 comprises up to 10% ethyl alcohol by weight.

24. The composition of claim 1, wherein Part 2 comprises 20–80% water by weight.

25. The composition of claim 1, wherein the Part 1 and Part 2 are mixed together less then about 20 minutes before application.

26. A teeth whitening procedure, comprising:
   preparing a teeth whitening composition comprising mixing a first part comprising 5–40% by weight of at least one metal peroxide and a second part comprising at least one acid to form a material having a pH of about 4 to 11; and
   applying the teeth whitening composition to the teeth.

27. The teeth whitening procedure of claim 26, wherein the teeth whitening composition is applied to the teeth by means of flexible trays or forms.

28. The teeth whitening procedure of claim 26, wherein the teeth whitening composition is applied to the teeth by means of a toothbrush.

29. The teeth whitening procedure of claim 26, wherein the teeth whitening composition is delivered to the teeth by means of freehand technique.

30. The teeth whitening procedure of claim 26, wherein the duration of contact of the teeth whitening composition with the teeth in a single session is between 2–120 minutes.

31. A teeth whitening composition comprising:
   Part 1 comprising 5–40% by weight of at least one metal peroxide; and
   Part 2 comprising at least one acid;
      wherein the Part 1 and Part 2 are mixed together before application to form a material comprising hydrogen peroxide and having a pH of about 4 to 11.

32. A composition for whitening teeth, comprising:

a first part comprising 5–40% by weight of at least one metal peroxide; and a second part comprising at least one acid;

wherein the first part and second part are thermally stable and wherein mixing the first and second parts prior to application to the teeth results in the in situ generation of hydrogen peroxide.

33. A method for whitening teeth, comprising preparing a teeth whitening composition having a pH of about 4 to 11 by mixing a first part comprising 5–40% by weight of at least one metal peroxide and a second part comprising at least one acid, the mixing of which generates hydrogen peroxide in situ;

applying the teeth whitening composition to the teeth.

* * * * *